United States Patent [19]

Panza et al.

[11] Patent Number: 4,801,480
[45] Date of Patent: Jan. 31, 1989

[54] COMPOSITE PRELAMINATED TAPE SYSTEM

[75] Inventors: Victor F. Panza; Alejandro Rosso; Daniel A. Gayuli, all of Buenos Aires, Argentina

[73] Assignee: Minnesota Mining and Manufacturing Company, St. Paul, Minn.

[21] Appl. No.: 116,168

[22] Filed: Nov. 3, 1987

[51] Int. Cl.$^4$ ............................ B32B 3/06; B32B 7/02
[52] U.S. Cl. .................................... 428/40; 428/354; 428/906; 604/390
[58] Field of Search ................. 428/40, 354, 906; 604/390, 389

[56] References Cited

U.S. PATENT DOCUMENTS

| | | | |
|---|---|---|---|
| 3,616,114 | 10/1971 | Hamaguchi | 428/41 |
| 4,047,528 | 9/1977 | Karami | 604/390 |
| 4,726,971 | 2/1988 | Pape et al. | 428/40 |

Primary Examiner—Alexander S. Thomas
Attorney, Agent, or Firm—D. M. Sell; C. Truesdale

[57] ABSTRACT

A composite adhesive tape system for interconnecting surfaces, parts and the like which includes a main fastening tape portion coated with an aggressive, tacky adhesive, a target tape portion and a release tape portion which covers the target tape portion and a centrally located layer which covers part of the release tape and partly folds under the target tape portion and methods for manufacturing and using the tape system as described. This system is particularly useful for providing novel prelaminated tape systems for diapers.

4 Claims, 2 Drawing Sheets

COMPOSITE PRELAMINATED TAPE SYSTEM

BACKGROUND OF THE INVENTION

This invention relates to composite prelaminated tapes for forming closures for disposable diapers which can be opened and refastened without destroying either the diaper or the tape.

At least as early as 1955, it had been suggested to use strips of normally tacky and pressure-sensitive adhesive tape to secure conventional cloth diapers on an infant; see, e.g., Chambers U.S. Pat. No. 2,714,889 and Ekberg U.S. Pat. No. 3,221,738. A few years later, when disposable diapers became extremely popular, strips of pressure-sensitive adhesive tape were again employed as closures; see, e.g., Gellert U.S. Pat. No. 3,620,217.

A disposable diaper typically has a thin, flexible, low density polyethylene film cover, an absorbent filler inside of the cover, and a porous inner liner overlying the filler. The diaper is positioned at the crotch of an infant with the two ends of the diaper extending toward the front and back respectively. Edges on each side of the diaper are then either positioned adjacent to each other or overlapped with a strip of pressure-sensitive adhesive tape being adhered to the cover at the border adjacent each of the two edges and holding the diaper closed.

After a tape closure has been opened, it is frequently discovered that the diaper has not been soiled and hence that there is no need to replace it. If the diaper cover has not been torn, a second strip of tape can sometimes be applied as a replacement closure, but this is often inconvenient. As a result, considerable work has been undertaken to develop a tape diaper closure that is not only capable of bonding firmly to the diaper cover but is also capable of being opened without destroying the tape diaper closure or the diaper cover and subsequently reclosed. Closures of this type have generally involved a combination of two or more tapes, one of which remains permanently adhered to one edge of the diaper and the other being removably adhered to the other edge of the diaper. Examples of such products are shown in Ness et al, U.S. Pat. No. 3,951,149; Milnamow U.S. Pat. No. 3,987,793; Feldman et al, U.S. Pat. No. 3,999,546; Richman et al, U.S. Pat. No. 4,020,842; and Schotz, U.S. Pat. No. 4,227,530.

Typically, tape closures for diapers are fabricated by positionably mounting a plurality of individual rolls of the appropriate tapes and combining them in situ to form a composite strip of tape, the width of which is substantially the same as the length of the diaper closure to be fabricated. The composite roll is then severed at right angles to the edges of the composite strip at intervals corresponding to the width of the desired tape closure and adhered at an appropriate location along the border adjacent the sides of the diaper as exemplified in Hamaguchi et al U.S. Pat. No. 3,616,114. Although this manufacturing process is effective, relatively sophisticated machinery is necessary to accomplish the superimposition of several rolls of tape to form a composite strip of tape in situ. Thus, it is desirable to provide diaper manufacturers with a composite prelaminated tape in a single roll from which closures may readily be prepared.

Commonly assigned copending U.S. patent application Ser. No. 891,131 of Pape et al describes a composite prelaminated tape comprising a pressure-sensitive adhesive fastening tape subdivided into bonded and fastening sections comprising a release tape, a fingerlift and a unifying strip. A problem which may be experienced with the Pape et al composite tape is the exposure of a small area of adhesive adjacent to the unifying strip which tends to adhere to the outer diaper cover and tear the cover upon opening of the closure. The present invention is an improvement over that invention.

SUMMARY OF THE INVENTION

The present invention provides novel composite prelaminated tapes for forming closures for disposable diapers of the type comprising a body of fluid-absorbing material having a fluid-impermeable polymeric foil outer cover, with a pressure-sensitive adhesive tape closure permanently mounted at a first border location adjacent one edge of the diaper and adapted for attachment to a second border location adjacent another edge when the two edge locations are juxtaposed or overlapped.

In accordance with the invention, the composite prelaminated tapes for forming the closures comprise a composite of
  (a) a pressure-sensitive adhesive fastening tape,
  (b) a fastening tape fingerlift,
  (c) a target tape,
  (d) a target tape fingerlift,
  (e) a release tape and
  (f) a unifying strip for both distributing tensile forces and to cover any exposed area of the fastening tape adhesive of the diaper.

The composite permits a portion of the fastening tape to be adhered permanently to an outer aspect of the diaper at a first border location and the remaining portion of the fastening tape and the target tape can be lifted from the release tape and adhered to a second border location such that when the fastening tape is lifted from the second border location, the target tape remains adhered to the second border location. The fastening tape can thereafter be repeatedly lifted from the target tape and re-adhered thereto. The unifying strip overlaps a portion of the fastening tape, thereby insuring the fastening tape does not tear the diaper cover by adhering to it.

Composite closures of the type just described are advantageously prepared from a roll of tape comprising a composite elongate strip of pressure-sensitive adhesive sheet material wound convolutely upon itself about an annular core. This composite strip is especially suited for preparing tape closures of the type described by simply severing the elongate strip of tape parallel to the axis of the core at intervals corresponding to the predetermined width of the closure.

BRIEF DESCRIPTION OF THE DRAWINGS

The invention can be more easily understood by referring to the accompanying drawings, in which certain dimensions are exaggerated to facilitate understanding. Like numbers refer to like parts in the several views, wherein.

DETAILED DESCRIPTION

Figure 1:
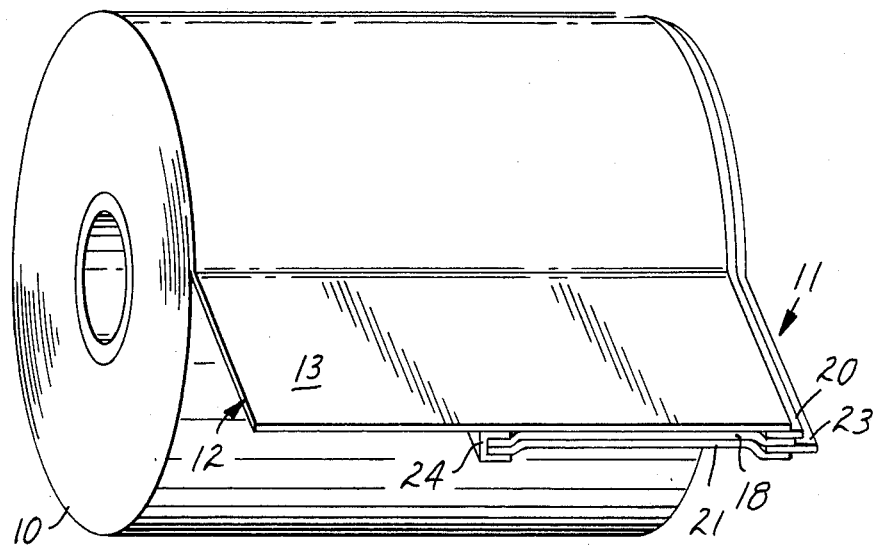
FIG. 1 shows a roll of composite tape suitable for use in practicing the invention.
Figure 2:
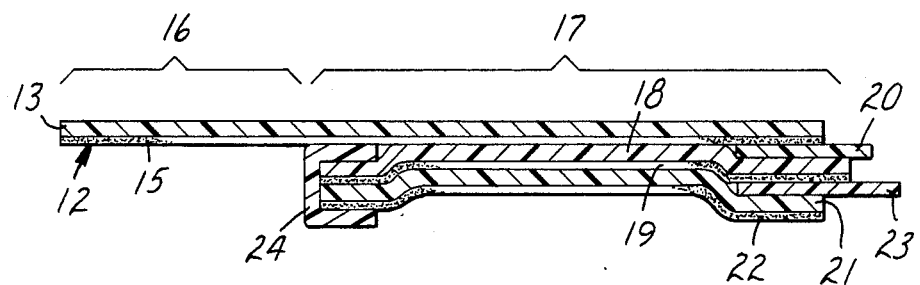
FIG. 2 is an enlarged cross-sectional view of the composite tape of FIG. 1.

In FIGS. 1 and 2, tape roll 10 is formed of composite tape 11 wound convolutely upon itself about a core. Composite tape 11 is subdivided into bonded section 16 and fastening section 17 and made up of fastening tape 12, target tape 18, release tape 21 and unifying strip 24.

Fastening tape 12 comprises any suitable tape backing 13 such as treated creped paper, polymeric film, etc., typically provided with a coating of a suitable release agent to facilitate unwinding of the composite tape when wound upon itself about the core. In one embodiment of the invention, one face of the backing 13 is coated with a layer 15 of a tacky and aggressive pressure-sensitive adhesive. Suitable adhesives include conventional rubber-resin adhesives which have tack characteristics modified by the inclusion of tackifying resins such as those described in U.S. Pat. No. 4,136,071. The aggressive pressure-sensitive adhesives used for layer 15 may also include conventional rubber-resin adhesives modified to have peel strengths between about 6 and 10 newtons per 25 mm, preferably about 8 newtons per 25 mm. A suitable method for measuring the peel strengths of adhesive layers on a steel, polyethylene or polypropylene surface is described hereinbelow.

Description of Test Procedure

90° Peel Adhesion. A 330-micrometer thick sheet of low density polyethylene (e.g., Eastman 1550 P-16421) is cast on a highly polished chrome roll and cooled to room temperature. Test samples approximately 80 mm×300 mm are then cut from this polyethylene sheet and a highly aggressive double-coated pressure-sensitive adhesive tape is used to bond the non-shiny surface of the polyethylene to a smooth steel panel. A 25 mm×300 mm specimen of tape to be evaluated as a potential diaper closure is then obtained and the adhesive surface is placed in contact with the shiny surface of the polyethylene sheet and forced into intimate contact with one forward and back pass of a mechanically operated 100 g roller. Within one minute thereafter the steel test panel is then mounted in the lower jaw of an "Instron" tensile testing machine with the tape surface upward. The free end of the tape strip is then mounted in the upper jaw of the tensile testing machine and pulled upward at 90°. The upper and lower jaws are separated at a rate of approximately 300 mm/min., noting the average force required for removal.

Target tape 18, formed of any suitable tape backing material, is positioned so that it coincides with and covers part of adhesive layer 15. The top surface of target tape 18 is releasably adhered to adhesive layer 15 except in the center of the tape roll where a portion of unifying strip 24 is located between adhesive layer 15 and target tape 18. The bottom surface of target tape 18 is coated with a layer 19 of normally tacky and pressure-sensitive adhesive. This adhesive layer 19 must form a strong shear bond to the outer surface of the diaper where it is adhered during use and may be the same as adhesive layer 15.

A first fingerlift 20 is positioned between fastening tape 12 and target tape 18. The first fingerlift 20 is adhered to fastening tape 12 by adhesive layer 15. Fingerlift 20 facilitates the lifting of fastening tape 12 from the target tape 18.

Release tape 21, formed of any suitable tape backing material, is positioned such that it substantially covers, and is adhered to adhesive layer 19. The top surface of release tape 21 may be provided with a coating of release agent so that target tape 18 may be readily separated from release tape 21.

A second fingerlift 23 is adhesively attached to target tape 18 by adhesive layer 19. The fingerlift 23 is attached to an end portion of target tape 18 and facilitates the separation of target tape 18 from release tape 21 in order to allow initial positioning of target tape 18 and fastening tape 12 on the opposed side of the diaper.

Fingerlifts 20 and 23 which are typically formed of narrow strips of polymeric film, are adhered to backing 13 and target tape 18 by adhesive layers 15 and 19 respectively. The fingerlifts 20 and 23 extend outwardly beyond the edge of fastening tape 12 and target tape 18 to permit and facilitate the separation of the various tapes. The separation of fastening tape 12 from target tape 18 is facilitated to obtain the position shown in FIG. 5 when it is desired to reopen the diaper closure.

Unifying strip 24, typically formed of a narrow strip of the same material as fingerlifts 20 and 23 is positioned between end portions of tape 11 such that its centerline coincides with the junction of target tape 18 and release tape 21 and adhesive layers 15, 19 and 22. Thus, one part of unifying strip 24 is adhered to adhesive layer 22 and an approximately equal part is adhered to adhesive layer 15 with target tape 18 and release tape 21 layered between as shown most clearly in FIG. 2.

Figure 3:
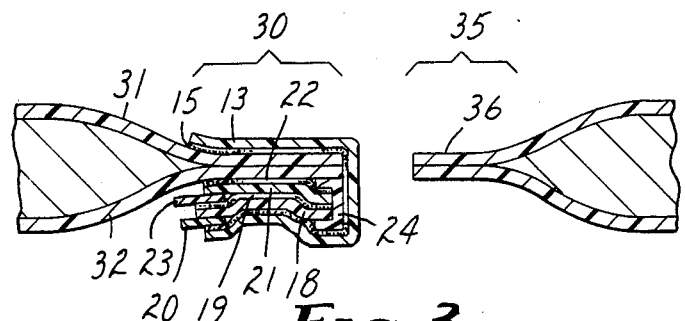
FIG. 3 is an enlarged cross-sectional view showing juxtaposed diaper edges, a closure formed from the tape of FIGS. 1 and 2 applied to one of the edges.
Figure 4:
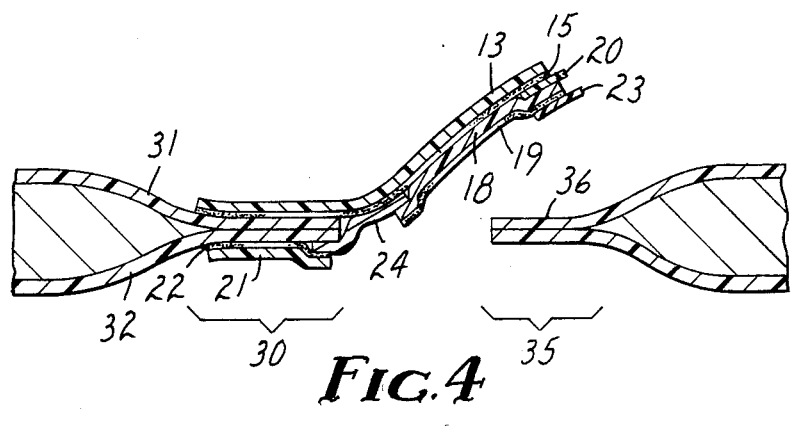
FIG. 4 is an enlarged cross-sectional view showing the tape closure ready to close two juxtaposed diaper edges.
Figure 5:
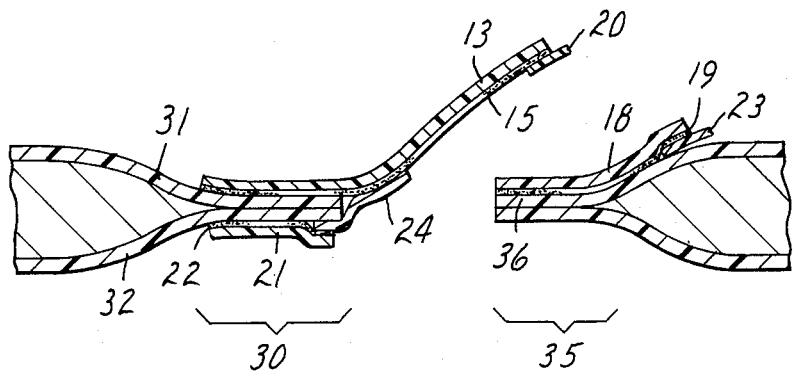
FIG. 5 is an enlarged cross-sectional view showing how the tape closure is opened without destroying either the tape or the diaper leaving the target tape in place.

As previously indicated, FIGS. 3–5 illustrate the use of closures formed by severing composite tape 11 at intervals corresponding to the predetermined width of the closure, parallel to the axis of the tape core. Thus, in FIG. 3, diaper edges 30 and 35 are juxtaposed with surfaces 31 and 36 corresponding to the outer surface of a diaper cover, conventionally made of low density polyethylene film. As shown in FIGS. 2 and 3, adhesive layer 15 forming bonded section 16 of fastening tape 12 is adhered to diaper cover 31 in the area immediately adjacent the edge 30. Unifying strip 24 overlies and extends onto adhesive surface 15 and extends onto interior surface 32 of the diaper as held by adhesive layer 22. Adhesive layer 22 must form a strong shear bond to diaper surface 32 and may be the same as either adhesive layer 15 or adhesive layer 19.

As shown in FIG. 3, release tape 21 is permanently adhered to the inner surface 32 of diaper edge 30. Overlying and adhered to the back surface of both unifying strip 24 and release tape 21 is target tape 18. Because of the presence of a release agent on the back surface of release tape 21, target tape 18 may be separated from release tape 21 by grasping fingerlift 23 and pulling upwardly, away from tape 21. Tape 18 is then permanently adhered to the outer surface 36 of diaper edge 35 by placing the fastening section 17 of tape 12 onto the outer surface 36, thereby adhering tape 18 to the outer surface 36 by adhesive layer 19. The fastening tape 12 is thereafter separated from the target tape by grasping fingerlift 20 and pulling upwardly, yielding the arrangement shown in FIG. 5.

It will be observed, especially in FIG. 4, that when the diaper edges 30 and 35 are placed in a tensional relationship from the movement of a diapered baby, the tensional forces place fastening tape 12 in shear. The shear forces on one end of fastening tape 12 are then divided to the bottom surface 32 of diaper edge 30 and the top surface 31 of diaper edge 30 through unifying strip 24 due to the adhesive attachment of unifying strip 24 to fastening tape 12 and release tape 21. The division of the shear forces to the two surfaces 31 and 32 of diaper edge 30 substantially diminishes the likelihood of the tape closure being pulled off diaper edge 30 by tearing the film forming either target tape 18 or surfaces 31 and 32.

When it is desired to reopen the diaper closure, the end of fastening tape 12 is lifted free, by grasping fingerlift 20 off target tape 18 to which it bonds firmly enough to prevent inadvertent opening of the closure but not so firmly that it cannot be lifted free without tearing target tape 18. The unifying strip 24 protects the diaper cover 36 from exposure to adhesive layer 15, thereby insuring the diaper cover 36 will not be inadvertently torn upon opening of the diaper closure. Once lifted free, this end of fastening tape 12 can again be resealed by placing it in contact with the target tape 18; indeed the process can be successfully repeated many times.

We claim:

1. A roll of tape comprising an elongated prelaminated tape composite wound convolutely upon itself about an annular core, especially suited for preparing a tape closure for disposable diapers by simply severing said elongated prelaminated tape composite parallel to the axis of the core at intervals corresponding to the predetermined width of said closure, the length of each such closure corresponding to the width of the roll of tape, said prelaminated tape composite comprising in combination (a) a fastening tape divided into a bonded section and a fastening section with the fastening tape comprising an elongated strip of sheet backing material, having first and second edges, being substantially as wide as said tape composite, and having a first layer of normally tacky and pressure-sensitive adhesive coated over substantially one surface of said backing material;
   (b) a first fingerlift adhered to the first layer of pressure-sensitive adhesive adjacent the second edge thereof;
   (c) a target tape, having first and second surfaces, the first surface adhered to said first layer of the pressure-sensitive adhesive layer;
   (d) a second layer of normally tacky and pressure-sensitive adhesive coated on the second surface of the target tape;
   (e) a second fingerlift adhered to the second layer of normally tacky and pressure sensitive adhesive;
   (f) a release tape, having first and second surfaces, the first surface adhered to said second layer of pressure-sensitive adhesive layer;
   (g) a third layer of normally tacky and pressure-sensitive adhesive coated over the second surface of said release tape; and
   (h) a unifying strip centered over said release tape edge and adhered to the third adhesive layer and to the first adhesive layer on the fastening tape by folding under the target tape.

2. A roll of tape according to claim 1 wherein said first layer of normally tacky and pressure-sensitive adhesive has a peel strength of between about 6 and 10 newtons per 25 mm.

3. A roll of tape according to claim 1 wherein said second layer of normally tacky and pressure-sensitive adhesive has a peel strength of between about 6 and 10 newtons per 25 mm.

4. A roll of tape according to claim 1 wherein said third layer of normally tacky and pressure-sensitive adhesive has a peel strength of between about 6 and 10 newtons per 25 mm.

* * * * *